United States Patent [19]

Chekroun et al.

[11] Patent Number: 4,482,718

[45] Date of Patent: Nov. 13, 1984

[54] PROCESS FOR THE PREPARATION OF 2-(THIEN-2-YL)- AND 2-(THIEN-3-YL)-ETHYLAMINE DERIVATIVES

[75] Inventors: Isaac Chekroun, Toulouse; Alain Heymes, Sisteron, both of France

[73] Assignee: Sanofi, Toulouse, France

[21] Appl. No.: 393,387

[22] Filed: Jun. 29, 1982

[30] Foreign Application Priority Data

Jun. 30, 1981 [FR] France .................... 81 13062

[51] Int. Cl.³ .................. C07D 333/20; C07D 409/12
[52] U.S. Cl. ..................... 546/284; 260/944; 546/22; 546/114; 549/6; 549/59; 549/60; 549/61; 549/65; 549/68; 549/71; 549/74; 549/75; 564/14; 568/14
[58] Field of Search ............. 549/6, 59, 60, 61, 65, 549/68, 71, 74, 75; 546/22, 114, 284; 564/14; 568/14; 260/944

[56] References Cited

U.S. PATENT DOCUMENTS 2,983,729  5/1961  Meyer et al. .............. 546/284
4,075,340  2/1978  Maffrand .................. 546/114 X
4,127,580 11/1978  Braye ..................... 546/114

OTHER PUBLICATIONS

Parcor, Chemical Abstracts, vol. 90 (1979) 72159q.
Parcor, Chemical Abstracts, vol. 91 (1979) 56,977v.

*Primary Examiner*—Richard L. Raymond
*Attorney, Agent, or Firm*—Weiser & Stapler

[57] ABSTRACT

The present invention provides a process for the preparation of 2-(thien-2-yl)- and 2-(thien-3-yl)-ethylamine derivatives of the general formula:

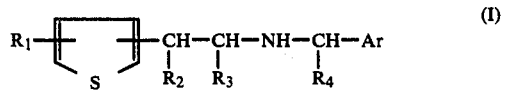

(I)

in which $R_1$, in the 2-, 3-, 4- or 5-position, is a hydrogen or halogen atom, a nitro, carboxyl, cyano or amino group, a linear or branched alkyl or alkoxy radical or a heterocyclic or non-heterocyclic aromatic radical, which is optionally mono- or polysubstituted, the aminoethyl chain is in the 2- or 3-position, $R_2$, $R_3$ and $R_4$, which are the same or different, are hydrogen atoms or heterocyclic or non-heterocyclic aromatic radicals, which are optionally mono- or polysubstituted, and Ar is a heterocyclic or non-heterocyclic aromatic radical, which is optionally mono- or polysubstituted.

13 Claims, No Drawings

PROCESS FOR THE PREPARATION OF 2-(THIEN-2-YL)- AND 2-(THIEN-3-YL)-ETHYLAMINE DERIVATIVES

The present invention is concerned with a new process for the preparation of thienylamines.

The thienylamines with which the present invention is concerned are compounds of the general formula:

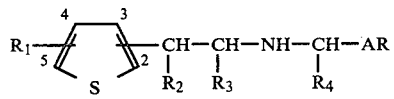
(I)

in which $R_1$, in the 2-, 3-, 4- or 5-position, is a hydrogen or halogen atom, a nitro, carboxyl, cyano or amino group, a linear or branched alkyl or alkoxy radical or a heterocyclic or non-heterocyclic aromatic radical, such as a thienyl, furyl, pyridyl, phenyl or naphthyl radical, optionally mono- or polysubstituted by substituents such as halogen, nitro, cyano, amino, carboxyl, alkyl, alkoxy or phenyl groups; the aminoethyl chain is in the 2- or 3-position of the thiophene nucleus; $R_2$, $R_3$ and $R_4$, which are the same or different, are hydrogen atoms, linear or branched alkyl radicals or a heterocyclic or non-heterocyclic aromatic radical, such as thienyl, furyl, pyridyl, phenyl or naphthyl radicals, optionally mono- or polysubstituted by substituents such as halogen, nitro, cyano, amino, carboxyl, alkyl, alkoxy or phenyl groups; and Ar is a heterocyclic or non-heterocyclic aromatic radical, such as a thienyl, furyl, pyridyl, phenyl or naphthyl radical, optionally mono- or polysubstituted by substituents such as halogen, nitro, cyano, amino, carboxyl, alkyl, alkoxy or phenyl.

A number of compounds according to general formula (I) are known and used as intermediates in the preparation of compounds employed both in the chemical industry and in the pharmaceutical industry.

Thus, by way of example, amongst the derivatives obtained in accordance with the new process, there may be mentioned those which can lead, by known means, on the one hand (when the aminoethyl chain is in the 2-position and the radical $R_1$ is in the 4- or 5-position) to 4,5,6,7-tetrahydrothieno[3,2-c]pyridine derivatives and, on the other hand (when the aminoethyl chain is in the 3-position and the radical $R_1$ is in the 4- or 5-position), to 4,5,6,7-tetrahydrothieno[2,3-c]pyridine derivatives; in both cases, these derivatives have formed the subjected of several of our earlier French Patents, namely, Nos. 73/03,503, 75/03,968, 75/20,241, 75/23,786, 75/24,486, 76/00,003, and 77/21,517, for their therapeutic use and/or processes for the preparation thereof.

The present invention provides a process, which is simple and inexpensive compared with the prior art, for the preparation of compounds of general formula (I).

According to the process of the present invention, the various steps thereof are as follows:

(a) a derivative of the general formula:

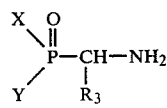
(II)

in which $R_3$ is as defined in general formula (I) and X and Y, which can be the same or different, are alkyl, aryl, alkoxy, aryloxy, dialkylamino or diarylamino radicals so that the organophosphorus compound of general formula (II) can be, for example, a phosphonate, a phosphinate, a phosphine oxide or a phosphonamide, is condensed with a carbonyl compound of the general formula:

(III)

in which Ar and $R_4$ are as defined in general formula (I), to give a compound of the general formula:

(IV)

in which X, Y, $R_3$, $R_4$ and Ar are as defined above;

(b) a compound of general formula (IV) is treated with a base of the general formula $B^\ominus M^\oplus$ to give a carbanion of the general formula:

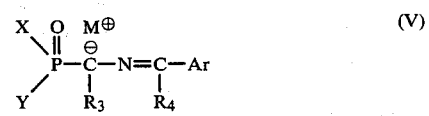
(V)

in which X, Y, $R_3$, $R_4$ and Ar are as defined above, this reaction being carried out at a temperature of from $-78°$ C. to $+100°$ C. which is chosen, more specifically as a function of the base $B^-M^+$, to be on the whole at the bottom of the range so as to avoid the formation of a compound of the general formula:

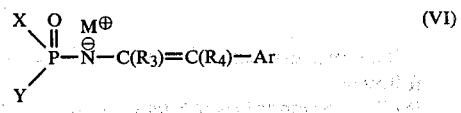
(VI)

(c) the carbanion of the general formula (V) is then reacted with a carbonyl derivative of the general formula:

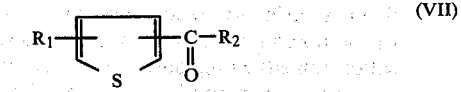
(VII)

in which $R_1$ and $R_2$ are as defined in general formula (I), to give a compound of the general formula:

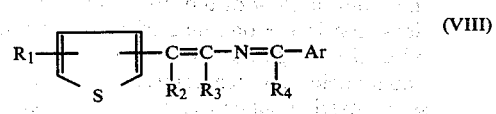
(VIII)

in which the substituents have the meanings given above;

(d) the compound of general formula (VIII) is finally converted, by reaction with a reducing agent, such as, in particular, an alkali metal borohydride, into a compound of general formula (I) as defined above.

The process according to the present invention can be illustrated by the following reaction scheme:

Stage (a)

-continued

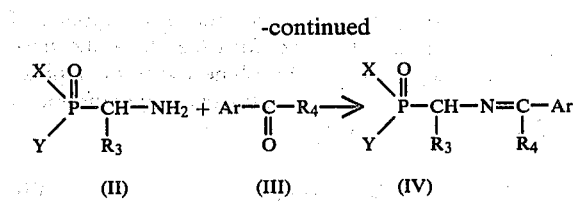

Stage (b)

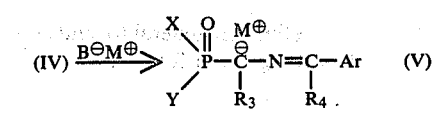

Stage (c)

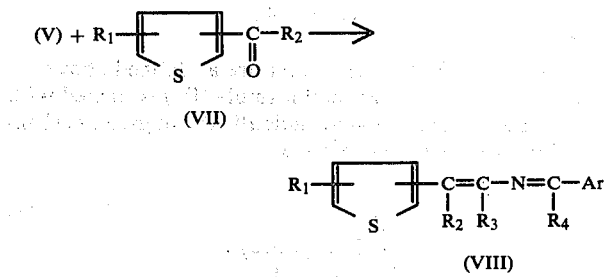

Stage (d)

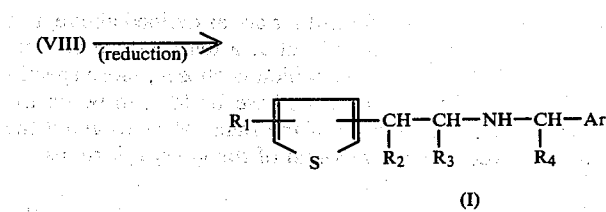

The process can advantageously be carried out as follows:

(a) The organophosphorus compounds of general formula (II), which are readily available by well known processes of preparation, such as the one described by I. C. Popoff et al. (J. Org. Chem., 28, 2898/1963), can be reacted with the carbonyl derivatives (III) in the absence of a solvent and of a catalyst, the water formed during the reaction being removed at the end of the operation by appropriate means. The condensation can advantageously be carried out in a solvent, such as an aromatic hydrocarbon, for example toluene, or an alcohol, for example ethanol, by means of which it is possible to remove the water by azeotropic distillation. It can also be advantageous (from the point of view of the speed) to carry out the condensation in the presence of a catalytic amount of a mineral or organic acid, for example, p-toluenesulphonic acid. The temperature at which this conversion is carried out can vary but is very generally from 20° to 120° C.

(b) The base B⊖M⊕ used can be an alkali metal hydride, especially sodium, lithium or potassium hydride, an alkali metal amide or alkylamide, especially an alkali metal dialkylamide, such as lithium diisopropylamide, or an organometallic compound, especially an organolithium, such as n-butyllithium, or an organosodium or organomagnesium. It is also possible to use alkali metal or alkaline earth metal alcoholates, such as sodium, lithium, potassium or magnesium methylate, potassium tert.-butylate or sodium tert.- amylate. It is also possible to use alkali metal or alkaline earth metal hydroxides, such as sodium, lithium, potassium or magnesium hydroxide.

In general, the base is used in a slight excess, for example in an excess of 10%, referred to the stoichiometric equivalence.

The reaction is generally carried out at a temperature of from −78° C. to +100° C., the temperature being chosen, more specifically, as a function of the base B⊖M⊕, to be on the whole at the bottom of the range so as to avoid the formation of a compound (VI), as already mentioned above.

The preferred solvents are linear or cyclic ethers, such as tetrahydrofuran, hydrocarbons, in particular aromatics, such as benzene, toluene and xylenes, alcohols, amides, in particular dimethylformamide, and sulphoxides, in particular dimethyl sulphoxide. It can also be advantageous, especially when using metal hydroxides, to carry out the reaction in a two-phase system (water+a solvent, such as a halogen-containing solvent, for example methylene chloride, or an aromatic hydrocarbon, for example benzene, toluene or xylenes) in the presence of a phase-transfer catalyst, especially a quaternary ammonium salt, such as tetra-n-butylammonium iodide, or a phosphonium salt.

(c) The compound (V) is reacted with the carbonyl compound (VII) in a reaction medium such as defined above, at a temperature of from −78° C. to +100° C., which is chosen, more specifically, as a function of the base B⊖M⊕, to be on the whole at the bottom of the range, for the reasons already mentioned above.

(d) The reduction of the compound (VIII) is advantageously carried out with a mixed alkali metal hydride, especially a borohydride, for example sodium borohydride or potassium borohydride. The reduction is carried out in an inert solvent, such as an ether, for example tetrahydrofuran or dioxan, or alternatively in an alcohol, for example methanol or ethanol. It can be advantageous, in certain cases, and especially when at least one of the symbols $R_2$, $R_3$ and $R_4$ is not a hydrogen atom, to add one molar equivalent, relative to the borohydride used, of an organic acid, for example acetic acid or trifluoroacetic acid, to the reaction mixture.

It is also possible to carry out this reduction by means of catalytic hydrogenation in a homogeneous or heterogeneous phase, under conditions which are generally well known.

The compounds of general formula (I) thus obtained can then be isolated and purified by usual methods. To carry out these operations, it can be advantageous to convert the free bases of general formula (I) into their salts, for example their acid-addition salts, by reaction with mineral or organic acids. The compounds of general formula (I) can be freed from their salts by known methods.

The present invention also includes the intermediates obtained in the various stages of the synthesis: compounds of the general formula:

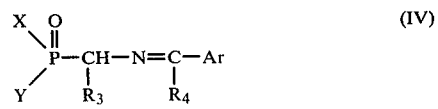

compounds of the general formula:

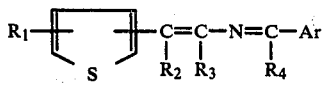

and compounds of the general formula:

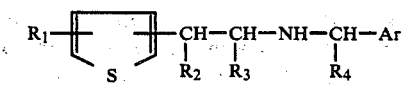

The following Examples are given for the purpose of illustrating the present invention:

EXAMPLE 1

Preparation of N-(o-chlorobenzyl)-2-(thien-2-yl)-ethylamine hydrochloride

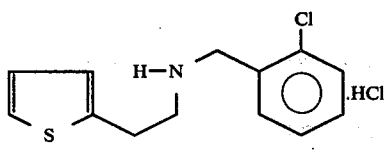

Stage a: Diethyl N-(o-chlorobenzylidene)-aminomethylphosphonate

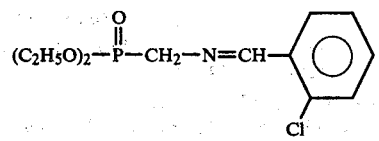

14 g. (0.1 mol) 2-chlorobenzaldehyde are added dropwise, at ambient temperature, to a solution of 16.7 g. (0.1 mol) diethyl aminomethylphosphonate in 200 ml. toluene. When the addition has ended, stirring is continued for 30 minutes. The water formed during the reaction is removed by decantation. The toluene phase is washed with 50 ml. of a saturated aqueous solution of sodium chloride, dried over anhydrous sodium sulphate and then evaporated. This gives 29 g. (yield: 100%) diethyl N-(o-chlorobenzylidene)-aminomethylphosphonate in the form of a yellow oil giving a single spot in TLC (silica plate, eluant: ethyl acetate, Rf=0.45).

IR (film): C=N, 1635 cm$^{-1}$, P=O, 1250 cm$^{-1}$, P—O—C, 1060–1030 cm$^{-1}$.

NMR (CDCl$_3$): δ/TMS, 1.35 ppm (t, 6H), 4.2 ppm (m, 6H), 7.1 to 7.5 ppm (m, 3H), 8 ppm (m, 1H), 8.7 ppm (d, 1H).

Stage b: 1-(2-Chlorophenyl)-4-(thien-2-yl)-2-azabuta-1,3-diene

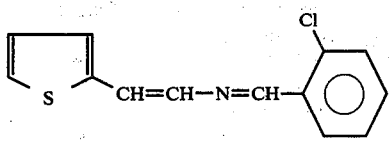

1.47 g. (4 millimols) tetra-n-butylammonium iodide are added to a vigorously stirred mixture of 50% aqueous sodium hydroxide solution and 80 ml. toluene and a solution of 28.95 g. (0.1 mol) of the imine prepared above and 11.2 g. (0.1 mol) thien-2-aldehyde in 20 ml. toluene is then added dropwise. After the end of the addition, during which the temperature rises from 20° to 35° C., the reaction mixture is heated at 40° C. for 30 minutes, with continued stirring.

After cooling and separation of the phases by decantation, the isolated aqueous phase is extracted twice with 50 ml. amounts of toluene. The combined organic phases are washed with water, dried over anhydrous sodium sulphate and then evaporated. This gives 19.8 g. (yield: 80%) 1-(2-chlorophenyl)-4-(thien-2-yl)-2-azabuta-1,3-diene in the form of a yellow oil giving virtually a single peak in GC (OV: 17).

IR (film): C=N 1640 cm$^{-1}$

NMR (CDCl$_3$): H,

8.6 ppm (s, 1H), 8 ppm (m, 1H), 6.9 to 7.9 ppm (m, 8H).

Stage c: N-(o-Chlorobenzyl)-2-(thien-2yl)-ethylamine hydrochloride

A solution of the above crude azadiene (19.8 g.) in 50 ml. ethanol is added dropwise, in the course of 5 minutes, to a solution of 6.08 g. (0.16 mol) sodium borohydride in 150 ml. ethanol. After the end of the addition, during which the temperature rises from 20° to 30° C., the reaction mixture is heated slowly to a temperature of from 45° to 50° C. and the reaction is left to continue at this temperature for one hour.

The reaction medium is then evaporated and the residue obtained is taken up in diisopropyl ether. The ether phase is washed several times with 1N sodium hydroxide solution and water, dried over anhydrous sodium sulphate and then evaporated to give 20 g. (yield: 100%) N-(o-chlorobenzyl)-2-(thien-2-yl)-ethylamine in the form of a light yellow oil.

8.3 ml. of 12N aqueous hydrochloric acid are added dropwise, at 50° C., to the resulting crude base suspended in 50 ml. water and the mixture is then heated to 90° C. Upon cooling, the homogeneous solution thus obtained precipitates crystals, which are filtered off, washed with softened water and then dried at 50° C. in vacuo. This gives 20.4 g. (yield: 71%, referred to the diethyl aminomethylphosphonate used in stage (a) N-(o-chlorobenzyl)-2-(thien-2-yl)-ethylamine hydrochloride in the form of white crystals; m.p. 143° C.

IR (KBr disc): 3400 cm$^{-1}$, 2900 to 2600 cm$^{-1}$, 1575 cm$^{-1}$, 1450 cm$^{-1}$.

NMR (d$_6$-DMSO): δ/TMS, 7 to 7.8 ppm (m, 8H), 3.35 ppm (s, 4H), 4.15 ppm (s, 2H), about 9 ppm (m, 2H) exchangeable with D$_2$O.

Analysis: C$_{13}$H$_{14}$ClNS.HCl (M.W. 288.236): calculated: C 54.16%; H 5.24%; N 4.85%; found: 54.07%; 5.31%; 4.80%

EXAMPLE 2

Preparation of N-(o-chlorobenzyl)-2-(thien-3-yl)ethylamine hydrochloride

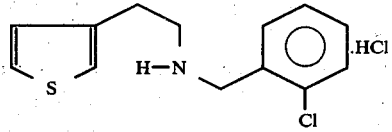

Stage a: Diethyl N-(o-chlorobenzylidene)-aminomethylphosphonate

By following the procedure of Example 1, using the same amounts, 29 g. (yield: 100%) of the desired product are obtained.

Stage b: 1-(2-Chlorophenyl)-4-(thien-3-yl)-2-azabuta-1,3-diene

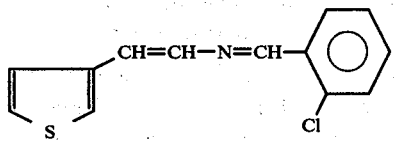

By following the procedure of Example 1 but using thien-3-aldehyde, 19.6 g. (yield: 79%) of the desired 2-azabuta-1,3-diene are obtained in the form of a yellow oil, after treatment, and this is reacted as such in the following stage.

Stage c: N-(o-Chlorobenzyl)-2-(thien-3-yl)-ethylamine hydrochloride

By following the procedure of Example 1 on the product prepared above, 19.2 g. (yield: 66%, referred to the diethyl aminomethylphosphonate used in stage a) are obtained in the form of white crystals; m.p. 176° C.

NMR (d$_6$-DMSO): δ/TMS, 3.2 ppm (s, 4H), 4.05 ppm (s, 2H), about 9 ppm (m, 2H), exchangeable with D$_2$O, 6.9 to 7.8 ppm (m, 7H).

IR (KBr disc): 3400 cm$^{-1}$, 2900 cm$^{-1}$, 2700–2800 cm$^{-1}$, 1575 cm$^{-1}$, 1450 cm$^{-1}$.

Analysis: C$_{13}$H$_{14}$ClNS.HCl (M.W. 288.236): calculated: C 54.16%; H 5.24%; N 4.85%; found: 54.13%; 5.30%; 4.82%

EXAMPLE 3

N-(Thien-2-yl)-methyl-2-(thien-2-yl)-ethylamine hydrochloride

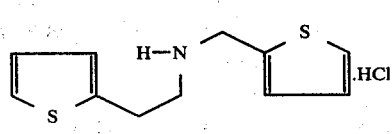

Stage a: Diethyl N-thien-2-ylidene-aminomethylphosphonate

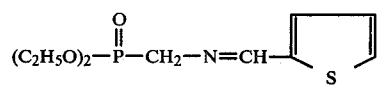

A solution of 16.7 g. (0.1 mol) diethyl aminomethylphosphonate in 200 ml. absolute ethanol is treated with 11.2 g. (0.1 mol) thien-2-aldehyde and the resulting mixture is heated under reflux and then evaporated to give 26 g. diethyl N-thien-2-ylidene-aminomethylphosphonate (yield: about 100%) in the form of a yellow oil giving a single spot in TLC (silica plate; eluant: ethyl acetate).

IR (film): C=N 1640 cm$^{-1}$, P=O 1260 cm$^{-1}$, P—O—C 1060–1080 cm$^{-1}$.

NMR (CDCl$_3$): δ/TMS, 1.35 ppm (t, 6H), 3.9 to 4.45 ppm (m, 6H), 7 to 7.8 ppm (m, 3H), 8.5 ppm (d, 1H).

Stage b: 1-(Thien-2-yl)-4-(thien-2-yl)-2-azabuta-1,3-diene

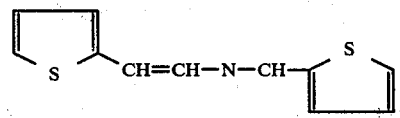

By carrying out the reaction under the conditions described in Example 1, 18.6 g. (yield: 85%) of the desired 2-azabuta-1,3-diene are obtained in the form of yellow crystals; m.p. 163° C.

IR (KBr disc) C=N 1635 cm$^{-1}$

NMR (d$_6$-DMSO): 8.35 ppm (s, 1H), 6.9 to 7.5 ppm (m, 8H).

Analysis: C$_{11}$H$_9$NS$_2$ (M.W. 219.322): calculated: C 60.27%; H 4.10%; N 6.39%; found: 60.25%; 4.07%; 6.40%

Stage c: N-(Thien-2-yl)-methyl-2-(thien-2-yl)-ethylamine hydrochloride 3.7 g. (0.1 mol) Sodium borohydride are added gradually to 10.95 g. (0.05 mol) of the 2-aza-1,3-diene obtained above, suspended in 100 ml. of ethanol, and the reaction mixture is heated to 40°–45° C. After stirring for 2 hours at this temperature, the mixture, which has become homogeneous and colourless, is worked up as in Example 1. The crude base obtained, dissolved in diisopropyl ether, is treated with a 4.5N solution of hydrogen chloride in the same solvent. The precipitate formed is filtered off, washed with diisopropyl ether and then dried at 50° C. in vacuo. This gives 11.15 g. (yield: 73%, referred to the diethyl aminomethylphosphonate) of N-(thien-2-yl)-methyl-2-(thien-2-yl)-ethylamine hydrochloride in the form of white crystals; m.p. 230° C. (decomposition).

IR (KBr disc): 3400 cm$^{-1}$, 2920 cm$^{-1}$, 2750 cm$^{-1}$, 1440 cm$^{-1}$, 1250 cm$^{-1}$.

NMR (d$_6$-DMSO): 6.9 to 7.5 ppm (m, 6H), 4.40 ppm (s, 2H), 3.2 ppm (m, 4H), 9 ppm (m, 2H), exchangeable with D$_2$O.

Analysis: C$_{11}$H$_{13}$NS$_2$.HCl (M.W. 259.813): calculated: C 50.86%; H 5.39%; N 5.39%; found: 50.90%; 5.40%; 5.37%

EXAMPLE 4

N-(o-Chlorobenzyl)-2-[5-tert.-butoxy-(thien-2-yl)]ethylamine

Stage a: Diethyl N-(o-chlorobenzylidene)-aminomethylphosphonate

The reaction is carried out using the same amounts and under the same conditions as in Example 1.

Stage b: 1-(2-Chlorophenyl)-4-[5-tert.-butoxy-(thien-2-yl)]-2-azabuta-1,3-diene 35.7 ml. of a 2.8M solution (0.1 mol) of n-butyllithium in hexane are added dropwise, at $-78°$ C. and under nitrogen, to a solution of 0.1 mol of the imine prepared above in 100 ml. of anhydrous tetrahydrofuran.

The solution, which has become dark red, is stirred for 30 minutes at $-78°$ C. and under nitrogen and then treated under the same conditions with a solution of 18.4 g. (0.1 mol) 5-tert.-butoxythien-2-aldehyde in 20 ml. of anhydrous tetrahydrofuran.

When the addition has ended, the yellow solution is stirred at ambient temperature for one hour and then evaporated in vacuo. The residue is taken up in water and then extracted twice with diisopropyl ether. The combined organic phases are dried over anhydrous sodium sulphate and then evaporated in vacuo to give 32 g. 1-(2-chlorophenyl)-4-[5-tert.-butoxy-(thien-2-yl)]-2-azabuta-1,3-diene in the form of a yellow oil, which is used as such in the following stage.

Stage c: N-(o-Chlorobenzyl)-2-[5-tert.-butoxy-(thien-2-yl)]ethylamine

Starting from 16 g. (0.05 mol) of the 2-azabuta-1,3-diene prepared above and 3.8 g (0.1 mol) sodium borohydride and following the procedure of Example 1, 13 g. of the desired amine are obtained in the form of a yellow oil, which is purified via its oxalate. This gives 8.9 g. (yield: 55%, referred to the ethyl aminomethylphosphonate) of N-(o-chlorobenzyl)-2-[5-tert.-butoxy-(thien-2-yl)]-ethylamine in the form of a light yellow oil; m.p. of the oxalate 202° C. (decomposition).

IR (film) of the base: 3300 cm$^{-1}$, 2850 to 3000 cm$^{-1}$, 1560 cm$^{-1}$, 1150 cm$^{-1}$.

NMR (CDCl$_3$) of the base: δ/TMS, 1.3 ppm (s, 9H) (CH$_3$)$_3$C, 1.7 ppm (s, 1H), exchangeable with D$_2$O, 2.8 ppm (s, 4H)

3.85 ppm (s, 2H) —N—CH$_2$—Ar, $\left.\begin{array}{l}\text{6.05 ppm (d, 1H)}\\\text{6.35 ppm (d, 1H)}\end{array}\right\}$ AB system, $J_{AB} = 4$ Hz 7.2 ppm (m, 4H).

Analysis: C$_{17}$H$_{22}$NClOS.C$_2$H$_2$O$_4$ (M.W. 413.91): calculated: C 55.13%; H 5.84%; N 3.39%; found: 55.02%; 5.87%; 3.37%

EXAMPLE 5

Preparation of N-(o-chlorobenzyl)-2-methyl-2-(thien-2-yl)-ethylamine hydrochloride

Stage a: Diethyl N-(o-chlorobenzylidene)-aminomethylphosphonate

By following the procedure of Example 1, 0.088 mol of the desired imine is prepared.

Stage b: 1-(2-Chlorophenyl)-4-(thien-2-yl)-4-methyl-2-azabuta-1,3-diene 23.4 ml. of a 25% (w/w) solution of n-butyllithium in hexane (0.088 mol) are added, with stirring, at $-78°$ C. and under nitrogen, to the imine prepared above (0.088 mol), dissolved in 100 ml. of anhydrous tetrahydrofuran. 11.1 g. (0.088 mol) 2-acetylthiophene in 20 ml. of tetrahydrofuran are added to the dark red solution at $-78°$ C. The reaction mixture is stirred for 2 hours at $-30°$ C. and then for 12 hours at ambient temperature, poured into a saturated aqueous solution of ammonium chloride and finally extracted 3 times with 100 ml. of methylene chloride. The combined organic phases are washed with water, dried over anhydrous sodium sulphate and evaporated to give an oily residue which solidifies upon trituration in diisopropyl ether to give 14.6 g. (yield: 63) 1-(2-chlorophenyl)-4-(thien-2-yl)-4-methyl-2-azabuta-1,3-diene in the form of yellow crystals giving a single spot in TLC; m.p. 102° C.

IR (KBr disc): 3040 cm$^{-1}$, 2940 cm$^{-1}$, 1620 cm$^{-1}$, 1580 cm$^{-1}$, 1540 cm$^{-1}$, 1465 cm$^{-1}$, 1435 cm$^{-1}$.

NMR (CDCl$_3$): δ/TMS, 2.2 ppm (s, 3H), 6.9 to 8.1 ppm (m, 8H), 8.75 ppm (d, 1H).

Mass spectrum: (1) under chemical ionisation (ammonia) (M+1)+ =262-4; (2) under electron impact (M−Cl)+ =226.

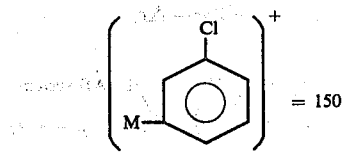 = 150

Stage c:
N-(o-Chlorobenzyl)-2-methyl-2-(thien-2-yl)-ethylamine hydrochloride Starting from 1 g. of the 2-azabuta-1,3-diene prepared above and following the procedure of the preceding Examples, 0.8 g. (yield: 70%, referred to the azadiene) of the desired hydrochloride is obtained in the form of white crystals; m.p. 120° C.

IR (KBr disc): 3400 cm$^{-1}$, 3000-2800 cm$^{-1}$, 1570 cm$^{-1}$, 1460 cm$^{-1}$.

NMR (d$_6$-DMSO): δ/TMS, 1.32 ppm (d, 3H), 3.05 ppm (d, 2H), 3.45 ppm (m, 1H), 4.1 ppm (s, 2H), 6.95 to 7.6 ppm (m, 7H), about 9 ppm (m, 2H), exchangeable with D$_2$O.

Mass spectrum: (1) under chemical ionisation (ammonia) (M+1)+ 266 268; (2) under electron impact

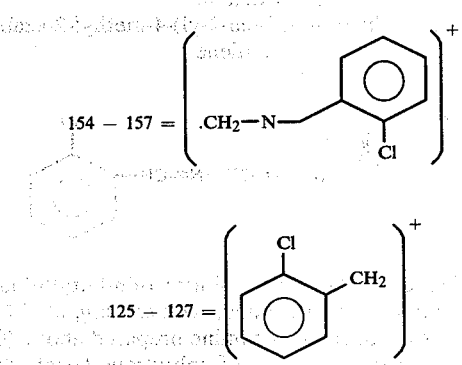

EXAMPLE 6
N-(o-Chlorobenzyl)-1-phenyl-2-(thien-2-yl)-ethylamine hydrochloride

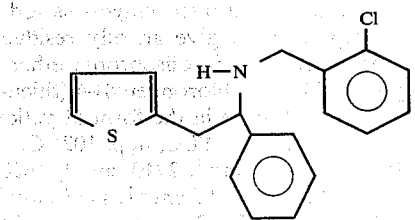

Stage a: Diethyl N-(o-chlorobenzylidene)-α-phenylaminomethylphosphonate

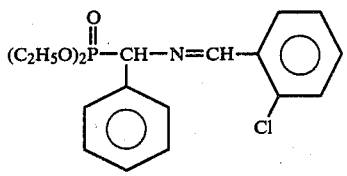

By following the procedure described in Example 3, starting from 12.15 g. (0.05 mol) diethyl α-phenylaminomethylphosphonate and 7.02 g. (0.05 mol) o-chlorobenzaldehyde, 18.3 g. (yield: 100%) of the desired product are obtained in the form of a light yellow oil giving a single spot in TLC.

IR (film): 2920 to 3100 cm$^{-1}$, 1635 cm$^{-1}$, 1250 cm$^{-1}$, 1030 to 1050 cm$^{-1}$, 970 cm$^{-1}$.

NMR (CDCl$_3$): δ/TMS, 1.2 ppm (t, 6H), 3.9 ppm (m, 4H), 4.8 ppm (d, 1H), 7–7.8 ppm (m, 8H), 8.1 ppm (m, 1H), 8.65 ppm (d, 1H).

Stage b:
1-(2-Chlorophenyl)-3-phenyl-4-(thien-2-yl)-2-azabuta-1,3-diene

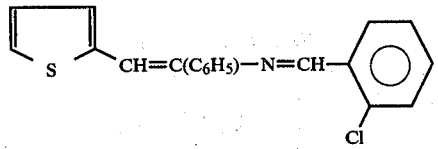

3.6 ml. (0.1 mol) of a 2.8M solution of n-butyllithium in hexane are added, with stirring, at −78° C. and under nitrogen, to 3.65 g. (0.01 mol) of the imine prepared above, dissolved in 50 ml. of anhydrous tetrahydrofuran. After stirring for a further 30 minutes, a solution of 1.12 g. (0.01 mol) thien-2-aldehyde in 20 ml. tetrahydrofuran is added, still at −78° C. The reaction mixture is subsequently stirred for 2 hours at ambient temperature and then evaporated. The residue is taken up in a mixture of water and chloroform. The isolated organic phase is washed several times with water, dried over anhydrous sodium sulphate and evaporated to give an oil which solidifies upon trituration in methanol to give 1.68 g. (yield: 52%) of the desired 2-azabuta-1,3-diene in the form of yellow crystals; m.p. 118° C.

IR (KBr disc): 3000-3100 cm$^{-1}$, 1620 cm$^{-1}$, 1470-1440 cm$^{-1}$, 1265 cm$^{-1}$.

NMR (CDCl$_3$): δ/TMS, 8.85 ppm (s, 1H), 6.95 to 8.1 ppm (m, 13H).

Mass spectrum: (1) under chemical ionisation (ammonia) (M+1)+: 324-326; (s) under electron impact M+: 323-325 (M−Cl)+: 288.

Stage c:
N-(o-Chlorobenzyl)-1-phenyl-2-(thien-2-yl)-ethylamine hydrochloride 0.57 g. (0.015 mol) Sodium borohydride is added, with stirring, to a solution of 1 g. (0.003 mol) of the 2-azabuta-1,3-diene prepared above, in 20 ml. dioxan. The suspension is cooled to 0° C. and 1.15 ml. (0.015 mol) trifluoroacetic acid are then added dropwise at this temperature. After heating under reflux for 2 hours, the reaction mixture, which has become homogeneous, is poured into water, after cooling, and then extracted with chloroform. The isolated organic phase is washed several times with water, dried over anhydrous sodium sulphate and then evaporated to give a pale yellow oil, which is converted into the hydrochloride in an ethanolic medium to give 0.58 g. (yield: 52%, referred to the azadiene) of N-(o-chlorobenzyl)-1-phenyl-2-(thien-2-yl)-ethylamine hydrochloride in the form of white crystals; M.p. 214° C.

IR (KBr disc): 3400 cm$^{-1}$, 2950-2700 cm$^{-1}$, 1565-1450 cm$^{-1}$.

NMR (d$_6$-DMSO): 3.1 ppm (d, 2H), 4.95 ppm (t, 1H), 4.2 ppm (s, 2H), 6.9 to 7.95 ppm (m, 12H), about 9 ppm (m, 2H), exchangeable with D$_2$O.

Mass spectrum: (1) under chemical ionisation (ammonia) (M+1)$^+$ 328-330; (2) under electron impact

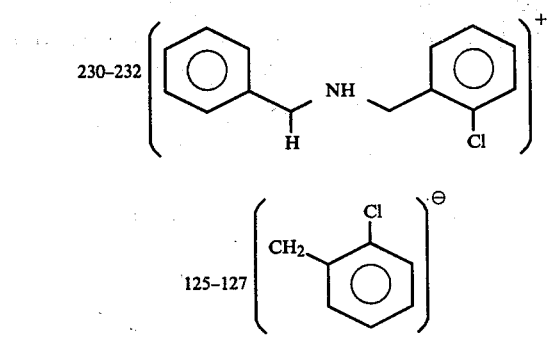

230-232

125-127

EXAMPLE 7
N-furfuran-2-yl-2-(thien-2-yl)-ethylamine oxalate

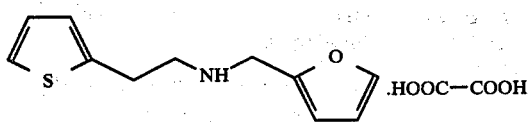

Stage a: Diethyl N-furfuran-2-ylidene-aminomethylphosphonate

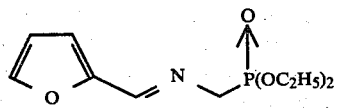

0.1 mol of the desired product is obtained in the form of a yellow oil by following the procedure described in Example 1.

IR (film): 1645 cm$^{-1}$, 1250 cm$^{-1}$, 1060 cm$^{-1}$, 1050 cm$^{-1}$.

NMR (CDCl$_3$): δ/TMS, 1.3 ppm (t, 6H), 4 ppm (m, 6H), 7 to 7.5 ppm (m, 3H), 8.3 ppm (d, 1H).

Stage b: 1-(Furan-2-yl)-4-(thien-2-yl)-2-azabuta-1,3-diene

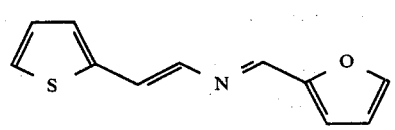

35.7 ml. of a 2.8M solution (0.1 mol) of n-butyllithium in hexane are added dropwise, at −78° C. and under nitrogen, to a solution of 0.1 mol of the imine prepared above, in 100 ml. of anhydrous tetrahydrofuran.

The solution is stirred for 30 minutes at −78° C. and under nitrogen and then treated under the same conditions with a solution of 11.2 g. (0.1 mol) thien-2-aldehyde in 20 ml. anhydrous tetrahydrofuran.

When the addition has ended, the solution is stirred at ambient temperature for 1 hour and then evaporated in vacuo. After being taken up in water, the residue is extracted with diisopropyl ether. The combined organic phases are dried over anhydrous sodium sulphate and then evaporated in vacuo to give 22 g. 1-(furan-2-yl)-4-(thien-2-yl)-2-azabuta-1,3-diene in the form of a yellow oil, which is used as such in the following stage.

Stage c: N-Furfuran-2-yl-2-(thien-2-yl)-ethylamine oxalate

Starting from the azadiene prepared above and 7.6 g. (0.2 mol) sodium borohydride and following the procedure of Example 1, the desired amine is obtained in the form of a yellow oil and purified via its oxalate, there being obtained 17.3 g. (yield: 58%, referred to the diethyl aminomethylphosphonate) N-(furfuran-2-yl)-2-(thien-2-yl)-ethylamine oxalate in the form of crystals; m.p. 215° C.

IR (KBr disc): 3400 cm$^{-1}$, 3040 cm$^{-1}$, 2850 cm$^{-1}$, 1715 cm$^{-1}$, 1650 cm$^{-1}$, 1480 cm$^{-1}$.

NMR (CDCl$_3$, on the base freed from the oxalate): δ/TMS, 1.65 ppm (s, 1H), exchangeable with D$_2$O, 2.8 ppm (s, 4H)

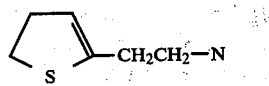

3.65 ppm (s, 2H)

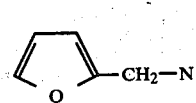

6.1 ppm (m, 2H), 6.6 to 7.3 ppm (m, 4H).

Analysis: C$_{11}$H$_{13}$NOS.C$_2$H$_2$O$_4$ (M.W. 297.324): calculated: C 52.52%; H 5.05%; N 4.71%; found: 52.50%; 5.03%; 4.65%.

EXAMPLE 8
N-(Picolin-4-yl)-2-(thien-2-yl)-ethylamine

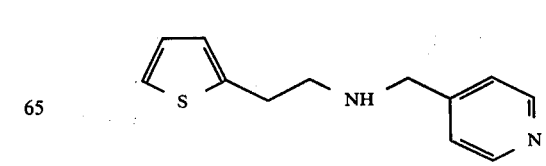

Stage a: Imine of pyridin-4-yl-carboxaldehyde and isopropyl aminomethyl-phenylphosphinate

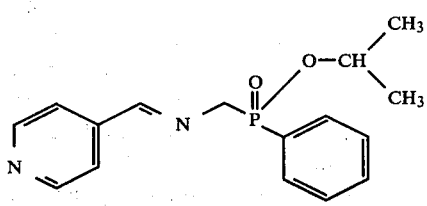

0.1 mol of the desired product is obtained in the form of a yellow oil by following the procedure described in Example 1.

IR (film): 3000 cm$^{-1}$, 1630 cm$^{-1}$, 1600 cm$^{-1}$, 1200 cm$^{-1}$, 980 cm$^{-1}$.

NMR (CDCl$_3$): δ/TMS, 1.4 ppm (dd, 6H), 4.15 ppm (d, 2H), 4.7 ppm (m, 1H), 7 to 7.8 ppm (m, 7H), 8.25 ppm (d, 1H), 8.55 ppm (d, 2H).

Stage b: 1-(Pyridin-4-yl)-4-(thien-2-yl)-2-azabuta-1,3-diene

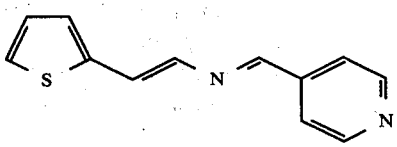

By following the procedure described in Example 7, 18.2 g. (yield: 85.3%) of the desired azadiene are obtained in the form of an orange oil, which is used as such in the following stage.

Stage c: N-(Picolin-4-yl)-2-(thien-2-yl)-ethylamine

Starting from the azadiene prepared above and 7.6 g. (0.2 mol) sodium borohydride and following the procedure of Example 1, the desired amine is obtained in the form of a brown oil which is purified by chromatography on a silica column. This gives 9.17 g. (yield: 42%, referred to the aminomethylphosphinate) N-(picolin-4-yl)-2-(thien-2-yl)-ethylamine in the form of a slightly coloured oil.

IR (film): 3300 cm$^{-1}$, 2900 cm$^{-1}$, 1600 cm$^{-1}$, 1440 cm$^{-1}$.

NMR (CDCl$_3$): δ/TMS, 1.7 ppm (s, 1H), exchangeable with D$_2$O, 3 ppm (t, 4H) Ar—CH$_2$—CH$_2$, 3.8 ppm (s, 2H) Ar—CH$_2$—N, 6.6 to 7.4 ppm (m, 5H), 8.4 ppm (d, 2H).

EXAMPLE 9

N-(o-Nitrobenzyl)-2-(thien-2-yl)-ethylamine hydrochloride

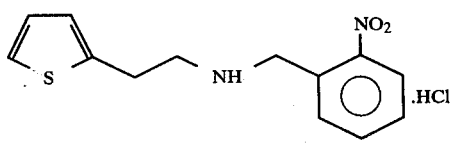

Stage a: Isopropyl N-(o-nitrobenzylidene)-aminomethylphenylphosphinate

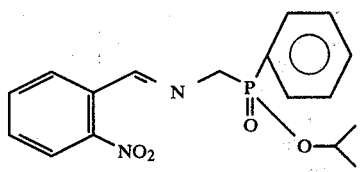

Starting from 0.1 mol o-nitrobenzaldehyde and 0.1 mol isopropyl aminomethyl-phenylphosphinate, 0.1 mol (100%) of the desired imine is obtained (by following the procedure described in Example 1) in the form of a yellow oil.

IR (film): 1630 cm$^{-1}$, 1200 cm$^{-1}$, 980 cm$^{-1}$.

NMR (CDCl$_3$): 1.5 ppm (dd, 6H), 4.25 ppm (d, 1H), 7.5 to 8.3 ppm (m, 9H), 8.6 ppm (d, 1H).

Stage b: 1-(o-Nitrophenyl)-4-(thien-2-yl)-2-azabuta-1,3-diene

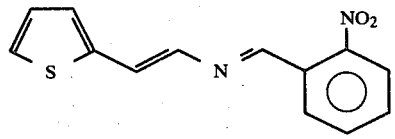

Starting from 0.1 mol of the imine prepared above and 0.1 mol thien-2-aldehyde and following the procedure described in Example 3, 22 g. of the desired azadiene (yield: 85%, referred to the aminomethylphosphinate) are obtained in the form of an oil, which is used as such in the following step.

Stage c: N-(o-Nitrobenzyl-2-(thien-2-yl)-ethylamine hydrochloride 6.46 g. (0.17 mol) sodium borohydride are added in small portions to the azadiene obtained above, dissolved in 200 ml. of ethanol, the temperature being kept below 25° C. The reaction mixture is subsequently stirred for 2 hours at ambient temperature and then poured into 1 liter water and extracted with chloroform. The organic phase is washed with water, dried over anhydrous sodium sulphate and then evaporated to give the base in the form of an oil, which is converted to the hydrochloride in ethanol. After recrystallisation of the precipitate formed from ethanol, 18.2 g. (yield: 61%, referred to the aminomethylphosphinate) of N-(o-nitrobenzyl)-2-(thien-2-yl)-ethylamine hydrochloride are obtained in the form of white crystals; m.p. 168° C.

IR (KBr disc): 3450 cm$^{-1}$–3000 cm$^{-1}$–2900 cm$^{-1}$, 2700 cm$^{-1}$, 1560 cm$^{-1}$–1525 cm$^{-1}$–1450 cm$^{-1}$, 1340 cm$^{-1}$.

NMR (CDCl$_3$, on the base freed from the hydrochloride): δ/TMS, 1.65 ppm (s, 1H), exchangeable with D$_2$O, 2.9 ppm (t, 4H), 4 ppm (s, 2H), 6.7 to 7.9 ppm (m, 7H).

Analysis: C$_{13}$H$_{14}$N$_2$O$_2$S.HCl (M.W. 298.773): calculated: C 52.26%; H 5.06%; N 9.36%; found: 52.28%; 5.03%; 9.31%.

EXAMPLE 10

N-(o-Chlorobenzyl)-2-(thienyl-2)-ethylamine hydrochloride

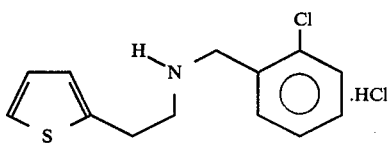

Stage a:
N-(o-Chlorobenzylidene)-aminomethyl-diphenylphosphine oxide

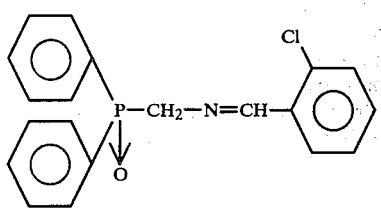

2.18 g. (0.015 mol) o-chlorobenzaldehyde is added dropwise to a solution of 3.5 g. (0.015 mol) aminomethyldiphenylphosphine in 150 ml. ethanol at ambient temperature. After evaporation of the solvent by heating to 50° C. under a slight vacuum, a clear yellow oil is obtained which is taken up hot in 50 ml. of a mixture of diisopropyl ether and ethanol (25/1 v/v). After cooling to 10° C., filtering and drying at 40° C. in vacuo, there are obtained 4.9 g. of crystals of the desired product; m.p. 89° C.

Stage b:
1-(2-Chlorophenyl)-4-(thienyl-2)-2-azabuta-1,3-diene

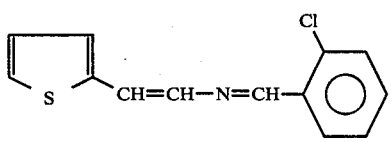

A solution of 2.65 g. (0.0075 mol) of the imine prepared above and 0.84 g. (0.0075 mol) thien-2-aldehyde in 8 ml. toluene is added dropwise to a vigorously stirred mixture of 10 g. of a 50% aqueous solution of sodium carbonate and 0.18 g. tetra-n-butylammonium iodide. Stirring is subsequently maintained for 1 hour at ambient temperature. The toluene phase isolated by decanting is washed with 50 ml. of a 2% aqueous solution of sodium chloride and then evaporated in vacuo. The residual oil obtained, after taking up in 6 ml. ethanol and cooling, becomes crystalline and the crystals are filtered off and dried in vacuo at ambient temperature. There is thus obtained 1.05 g. 1-(2-chlorophenyl)-4-(thienyl-2)-2-azabuta-1,3-diene; m.p. 65° C.

Stage c: N-(o-Chlorobenzyl)-2-(thienyl-2)-ethylamine

Operating as described in Example 1, starting from 0.45 g. of the azadiene obtained above and 0.2 g. sodium borohydride, there are obtained 0.4 g. of the desired compound; m.p. 143° C.

We claim:

1. Process for the preparation of 2-(thien-2-yl)- and 2-(thien-3-yl)-ethylamine derivatives of the general formula:

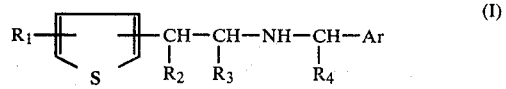

in which $R_1$, in the 2-, 3-, 4- or 5-position, is a hydrogen or halogen atom, a nitro, carboxyl, cyano or amino group, a linear or branched alkyl or alkoxy radical or a heterocyclic or non-heterocyclic aromatic radical, which is optionally mono- or polysubstituted, the aminoethyl chain is in the 2- or 3-position, $R_2$, $R_3$ and $R_4$, which are the same or different, are hydrogen atoms or heterocyclic or non-heterocyclic aromatic radicals, which are optionally mono- or polysubstituted, and Ar is a heterocyclic or non-heterocyclic aromatic radical, which is optionally mono- or polysubstituted, wherein a compound of the general formula:

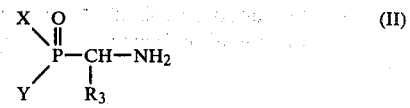

in which $R_3$ has the above-given meaning and X and Y, which may be the same or different, are alkyl, alkoxy, aryl, aryloxy, dialkylamino or diarylamino radicals, is condensed with a carbonyl compound of the general formula:

in which Ar and $R_4$ have the above-given meanings, to give a compound of the general formula:

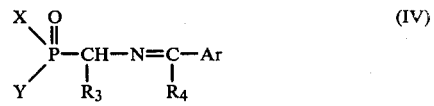

in which X, Y, Ar, $R_3$ and $R_4$ have the above-given meanings, which is treated with a base of the general formula $B^\ominus M^\oplus$ to give a carbanion of the general formula:

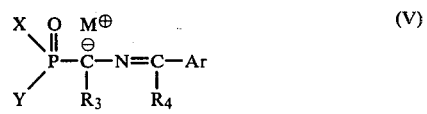

in which X, Y, Ar, $R_3$ and $R_4$ have the above-given meanings, which is reacted with a carbonyl derivative of the general formula:

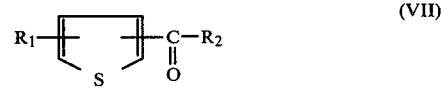

in which $R_1$ and $R_2$ have the above-given meanings, to give the compound of the general formula:

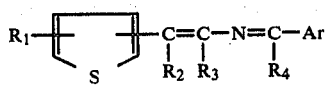 (VIII)

in which $R_1$, $R_2$, $R_3$, $R_4$ and Ar have the above-given meanings, which is treated with a reducing agent to give a compound of general formula (I).

2. Process according to claim 1, wherein the condensation reaction of the organophosphorus compound (II) with the carbonyl compound (III), in the case where the latter is a ketone ($R_4$ not H), is catalysed by the presence of a mineral or organic acid.

3. Process according to claim 2, wherein the acid is p-toluenesulphonic acid.

4. Process according to any of the preceding claims, wherein the formation of the carbanion in the presence of a base is carried out at a temperature of from $-78°$ C. to $+100°$ C.

5. Process according to claim 4, wherein the base used is an alkali metal hydride, an organomagnesium compound, an alkali metal alcoholate, an alkaline earth metal alcoholate, an alkali metal hydroxide or an alkaline earth metal hydroxide.

6. Process according to claim 4 or 5, wherein the reaction is carried out in an organic solvent.

7. Process according to claim 6, wherein the organic solvent is tetrahydrofuran, benzene or dimethyl sulphoxide.

8. Process according to any of claims 4 to 6, wherein the formation of the carbanion is carried out at a temperature which is chosen, as a function of the base, to be on the whole at the bottom of the range.

9. Process according to any of the preceding claims, wherein the reaction of the carbanion (V) with the carbonyl derivative (VII) is carried out at a temperature of from $-78°$ C. to $+100°$ C.

10. Process according to any of the preceding claims, wherein the hydrogenation reaction of the compound (III) is carried out with an alkali metal borohydride.

11. Process according to claim 10, wherein the alkali metal borohydride is sodium borohydride or potassium borohydride.

12. Process according to claim 10 or 11, wherein the reaction is carried out in an organic solvent.

13. Process according to claim 12, wherein the organic solvent is tetrahydrofuran, dioxan, methanol or ethanol.